(12) United States Patent
Koenig et al.

(10) Patent No.: US 11,737,458 B2
(45) Date of Patent: Aug. 29, 2023

(54) FIBROUS SUBSTRATE FOR CAPTURE OF GRAM NEGATIVE BACTERIA

(71) Applicant: Kimberly-Clark Worldwide, Inc., Neenah, WI (US)

(72) Inventors: David W. Koenig, Menasha, WI (US); Amy L. Vanden Heuvel, Hortonville, WI (US); Vinod Chaudhary, Appleton, WI (US); Scott W. Wenzel, Neenah, WI (US); Divesh Bhatt, Marietta, GA (US); Kathleen Engelbrecht, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 168 days.

(21) Appl. No.: 15/561,311

(22) PCT Filed: Apr. 1, 2015

(86) PCT No.: PCT/US2015/023813
§ 371 (c)(1),
(2) Date: Sep. 25, 2017

(87) PCT Pub. No.: WO2016/160006
PCT Pub. Date: Oct. 6, 2016

(65) Prior Publication Data
US 2018/0098536 A1      Apr. 12, 2018

(51) Int. Cl.
| | | |
|---|---|---|
| A01N 25/34 | (2006.01) | |
| A61K 31/717 | (2006.01) | |
| A61K 31/74 | (2006.01) | |
| D21J 1/16 | (2006.01) | |
| A61K 9/70 | (2006.01) | |

(52) U.S. Cl.
CPC ............ *A01N 25/34* (2013.01); *A61K 31/717* (2013.01); *A61K 31/74* (2013.01); *D21J 1/16* (2013.01); *A61K 9/70* (2013.01)

(58) Field of Classification Search
CPC ...... A01N 25/34; A61K 8/898; A61K 8/0208; A61K 9/70; A61K 9/7007
See application file for complete search history.

(56) References Cited

U.S. PATENT DOCUMENTS

| | | | |
|---|---|---|---|
| 3,303,048 A * | 2/1967 | Cooper et al. .... | D06M 15/6436 427/387 |
| 3,338,992 A | 8/1967 | Kinney | |
| 3,341,394 A | 9/1967 | Kinney | |
| 3,494,821 A | 2/1970 | Evans | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,007,113 A | 2/1977 | Ostreicher | |
| 4,100,324 A | 7/1978 | Anderson et al. | |
| 4,144,370 A | 3/1979 | Boulton | |
| 4,340,563 A | 7/1982 | Appel et al. | |
| 4,361,486 A | 11/1982 | Hou et al. | |
| 4,624,890 A | 11/1986 | Lloyd et al. | |
| 4,795,668 A | 1/1989 | Krueger et al. | |
| 5,057,361 A | 10/1991 | Sayovitz et al. | |
| 5,057,368 A | 10/1991 | Largman et al. | |
| 5,069,970 A | 12/1991 | Largman et al. | |
| 5,108,820 A | 4/1992 | Kaneko et al. | |
| 5,162,074 A | 11/1992 | Hills | |
| 5,277,976 A | 1/1994 | Hogle et al. | |
| 5,284,703 A | 2/1994 | Everhart et al. | |
| 5,336,552 A | 8/1994 | Strack et al. | |
| 5,350,624 A | 9/1994 | Georger et al. | |
| 5,382,400 A | 1/1995 | Pike et al. | |
| 5,413,789 A | 5/1995 | Hagiwara et al. | |
| 5,466,410 A | 11/1995 | Hills | |
| 5,512,186 A | 4/1996 | Wright et al. | |
| 5,593,599 A | 1/1997 | Wright et al. | |
| 5,736,058 A | 4/1998 | Wright et al. | |
| 5,742,943 A | 4/1998 | Chen | |
| 5,785,179 A | 7/1998 | Buczwinski et al. | |

(Continued)

FOREIGN PATENT DOCUMENTS

| | | |
|---|---|---|
| CN | 101856389 A | 10/2010 |
| CN | 102293802 A | 12/2011 |

(Continued)

OTHER PUBLICATIONS

WO2008/123115 Machine translation, to Misaki et al., Oct. 16, 2008, p. 1-7.*
Related U.S. Application Form.
Katsikogianni et al., "Concise Review of Mechanisms of Bacterial Adhesion to Biomaterials and of Techniques Used in Estimating Bacteria-Material Interactions" European Cells and Materials, vol. No. 8, University of Patras, Patras, Greece, 2004, pp. 37-57.
International Search Report for PCT/US2015/023813, dated Dec. 23, 2015, 11 pages.
Al-Waili et al., "Honey and microbial infections: a review supporting the use of honey for microbial control", J Med Food, Oct. 2011; 14 (10), 2 pages.
Hwang et al., "Resveratrol antibacterial activity' against *Escherichia coli* is mediated by Z-ring formation inhibition via suppression of FtsZ expression", Scientific Reports, vol. 5, Article No. 10029, 2015, 10 pages.

(Continued)

*Primary Examiner* — Tigabu Kassa
(74) *Attorney, Agent, or Firm* — Dority & Manning, P.A.

(57) ABSTRACT

A fibrous substrate for the removal of Gram negative bacteria (*Escherichia coli*) from a surface is provided. The fibrous substrate includes a capturing agent, and the affinity of capturing for the Gram negative bacteria allows the fibrous substrate to capture the Gram negative bacteria, thereby removing the Gram negative bacteria from the surface and also inhibiting the spread of the Gram negative bacteria to other surfaces that may contact the fibrous substrate. Of particular advantage, the presence of the capturing agent on the fibrous substrate may help protect against the spread or infection of pathogens without the use of chemicals, such as antiseptics or antibiotics.

19 Claims, No Drawings

(56) References Cited

U.S. PATENT DOCUMENTS

| | | | |
|---|---|---|---|
| 5,855,788 A | 1/1999 | Everhart et al. | |
| 5,908,707 A | 6/1999 | Cabell et al. | |
| 5,935,883 A | 8/1999 | Pike | |
| 5,942,219 A | 8/1999 | Hendriks | |
| 5,951,965 A | 9/1999 | Ansari et al. | |
| 5,964,351 A | 10/1999 | Zander | |
| 5,989,004 A | 11/1999 | Cook | |
| 6,030,331 A | 2/2000 | Zander | |
| 6,110,381 A | 8/2000 | Wright | |
| 6,123,996 A | 9/2000 | Larsson et al. | |
| 6,158,614 A | 12/2000 | Haines et al. | |
| 6,180,584 B1 | 1/2001 | Sawan et al. | |
| 6,200,669 B1 | 3/2001 | Marmon et al. | |
| 6,231,719 B1 | 5/2001 | Garvey et al. | |
| 6,241,898 B1 | 6/2001 | Wright et al. | |
| 6,248,880 B1 | 6/2001 | Karlson | |
| 6,267,996 B1 | 7/2001 | Bombardelli et al. | |
| 6,269,969 B1 | 8/2001 | Huang et al. | |
| 6,269,970 B1 | 8/2001 | Huang et al. | |
| 6,273,359 B1 | 8/2001 | Newman et al. | |
| 6,274,041 B1 | 8/2001 | Williamson et al. | |
| 6,294,186 B1 | 9/2001 | Beerse et al. | |
| 6,306,514 B1 | 10/2001 | Weikel et al. | |
| 6,315,864 B2 | 11/2001 | Anderson et al. | |
| 6,340,663 B1 | 1/2002 | Deleo et al. | |
| 6,515,095 B1 | 2/2003 | Omura et al. | |
| 6,565,749 B1 | 5/2003 | Hou et al. | |
| 6,569,828 B1 | 5/2003 | Thomas et al. | |
| 6,630,016 B2 | 10/2003 | Koslow | |
| 6,639,066 B2 | 10/2003 | Boström et al. | |
| 6,696,070 B2 | 2/2004 | Dunn | |
| 6,770,204 B1 | 8/2004 | Koslow | |
| 6,800,354 B2 | 10/2004 | Baumann et al. | |
| 6,838,005 B2 | 1/2005 | Tepper et al. | |
| 6,916,480 B2 | 7/2005 | Anderson et al. | |
| 6,946,196 B2 | 9/2005 | Foss | |
| 7,169,304 B2 | 1/2007 | Hughes et al. | |
| 7,192,601 B2 | 3/2007 | Walker | |
| 7,287,650 B2 | 10/2007 | Koslow | |
| 7,288,513 B2 | 10/2007 | Taylor et al. | |
| 7,384,762 B2 | 6/2008 | Drocourt et al. | |
| 7,432,234 B2 | 10/2008 | Ochomogo et al. | |
| 7,569,530 B1 | 8/2009 | Pan et al. | |
| 7,576,256 B2 | 8/2009 | Björnberg et al. | |
| 7,625,844 B1 | 12/2009 | Yang et al. | |
| 7,642,395 B2 | 1/2010 | Schroeder et al. | |
| 7,795,199 B2 | 9/2010 | Molinaro et al. | |
| 7,872,051 B2 | 1/2011 | Clarke | |
| 7,985,209 B2 | 7/2011 | Villanueva et al. | |
| 7,993,675 B2 | 8/2011 | Oliver et al. | |
| 8,030,226 B2 | 10/2011 | Bradley et al. | |
| 8,034,844 B2 | 10/2011 | Fox et al. | |
| 8,293,699 B2 | 10/2012 | Fütterer et al. | |
| 8,318,654 B2 | 11/2012 | Hoffman et al. | |
| 8,343,523 B2 | 1/2013 | Toreki et al. | |
| 8,481,480 B1 | 7/2013 | Lam et al. | |
| 8,506,978 B2 | 8/2013 | Soerens et al. | |
| 8,530,524 B2 | 9/2013 | Wegner et al. | |
| 8,603,771 B2 | 12/2013 | Stanley et al. | |
| 8,685,178 B2 | 4/2014 | Do et al. | |
| 8,771,061 B2 | 7/2014 | MacDonald | |
| 8,871,722 B2 | 10/2014 | Harding | |
| 9,006,163 B2 | 4/2015 | Hourigan et al. | |
| 9,511,206 B2 | 12/2016 | Hofius et al. | |
| 2001/0037100 A1* | 11/2001 | Shanklin | A61Q 19/00 604/358 |
| 2001/0040136 A1 | 11/2001 | Wei et al. | |
| 2001/0046525 A1 | 11/2001 | Bombardelli et al. | |
| 2002/0050016 A1 | 5/2002 | Willman et al. | |
| 2002/0189998 A1 | 12/2002 | Haase et al. | |
| 2003/0008791 A1 | 1/2003 | Chiang | |
| 2003/0069317 A1 | 4/2003 | Seitz, Jr. et al. | |
| 2003/0091540 A1 | 5/2003 | Ahmad et al. | |
| 2003/0162684 A1 | 8/2003 | Huyhn et al. | |
| 2004/0009141 A1 | 1/2004 | Koenig et al. | |
| 2004/0024374 A1 | 2/2004 | Hjorth et al. | |
| 2005/0130870 A1 | 6/2005 | Ochomogo et al. | |
| 2005/0137540 A1 | 6/2005 | Villanueva et al. | |
| 2005/0182021 A1 | 8/2005 | Nichols et al. | |
| 2005/0238612 A1 | 10/2005 | Courcoux et al. | |
| 2005/0242041 A1 | 11/2005 | Cumberland | |
| 2005/0244480 A1 | 11/2005 | Koenig et al. | |
| 2005/0271595 A1 | 12/2005 | Brown | |
| 2006/0134239 A1 | 6/2006 | Weide et al. | |
| 2006/0140899 A1 | 6/2006 | Koenig et al. | |
| 2006/0193789 A1 | 8/2006 | Tamarkin et al. | |
| 2006/0204466 A1 | 9/2006 | Littau et al. | |
| 2006/0205619 A1 | 9/2006 | Mayhall et al. | |
| 2006/0292086 A1 | 12/2006 | Curtis | |
| 2007/0020649 A1 | 1/2007 | Tseng et al. | |
| 2007/0048344 A1* | 3/2007 | Yahiaoui | C08K 5/31 424/405 |
| 2007/0001419 A1 | 6/2007 | Sayre et al. | |
| 2007/0207104 A1 | 9/2007 | Borish | |
| 2007/0237800 A1 | 10/2007 | Lahann | |
| 2007/0253926 A1 | 11/2007 | Tadrowski et al. | |
| 2007/0286894 A1 | 12/2007 | Marsh et al. | |
| 2008/0102053 A1 | 5/2008 | Childers | |
| 2008/0275113 A1 | 11/2008 | Huetter et al. | |
| 2008/0293613 A1 | 11/2008 | Johnson et al. | |
| 2008/0293826 A1 | 11/2008 | Rose et al. | |
| 2008/0312118 A1 | 12/2008 | Futterer et al. | |
| 2009/0004122 A1 | 1/2009 | Modak et al. | |
| 2009/0082472 A1 | 3/2009 | Peters | |
| 2009/0087465 A1 | 4/2009 | Doney et al. | |
| 2009/0155325 A1 | 6/2009 | Wenzel et al. | |
| 2009/0155327 A1 | 6/2009 | Martin et al. | |
| 2009/0191248 A1 | 7/2009 | Hoffman et al. | |
| 2009/0226498 A1 | 9/2009 | Flugge-Berendes et al. | |
| 2010/0135916 A1 | 6/2010 | Courel et al. | |
| 2010/0297029 A1 | 11/2010 | Biering et al. | |
| 2011/0009309 A1 | 1/2011 | Mertens et al. | |
| 2011/0081528 A1 | 4/2011 | Shannon et al. | |
| 2011/0091393 A1 | 4/2011 | Simmonds et al. | |
| 2011/0217345 A1* | 9/2011 | Huang | D21H 19/32 428/447 |
| 2011/0236447 A1 | 9/2011 | Yoshimura et al. | |
| 2011/0293681 A1 | 12/2011 | Berlin et al. | |
| 2012/0046362 A1 | 2/2012 | Kawahara et al. | |
| 2012/0121459 A1 | 5/2012 | Edgington et al. | |
| 2012/0164206 A1 | 6/2012 | Soerens et al. | |
| 2012/0207805 A1* | 8/2012 | Colman | A01N 33/12 424/404 |
| 2012/0269912 A1 | 10/2012 | Roberts et al. | |
| 2012/0294911 A1 | 11/2012 | Redmond et al. | |
| 2013/0037048 A1 | 2/2013 | Edgington et al. | |
| 2013/0079733 A1 | 3/2013 | Burt et al. | |
| 2013/0209576 A1 | 8/2013 | Brumeister et al. | |
| 2013/0274110 A1 | 10/2013 | Westbye et al. | |
| 2013/0287724 A1 | 10/2013 | Hoffman et al. | |
| 2014/0014584 A1 | 1/2014 | Cone et al. | |
| 2014/0147402 A1 | 5/2014 | Klug et al. | |
| 2014/0205546 A1 | 7/2014 | Macoviak | |
| 2014/0275255 A1 | 9/2014 | Pedersen et al. | |
| 2014/0301961 A1 | 10/2014 | Gillbro et al. | |
| 2014/0309173 A1 | 10/2014 | Dreher | |
| 2014/0356303 A1 | 12/2014 | Rocco et al. | |
| 2015/0010490 A1 | 1/2015 | Kim et al. | |
| 2015/0059795 A1 | 3/2015 | Vatter et al. | |
| 2015/0290102 A1 | 10/2015 | Cozean et al. | |
| 2016/0051452 A1* | 2/2016 | Nishizawa | A61Q 5/02 424/401 |
| 2017/0208798 A1 | 7/2017 | Chaudhary et al. | |
| 2017/0210900 A1 | 7/2017 | Engelbrecht et al. | |
| 2017/0224596 A1 | 8/2017 | Chaudhary et al. | |
| 2017/0303535 A1 | 10/2017 | Engelbrecht et al. | |

FOREIGN PATENT DOCUMENTS

| | | | |
|---|---|---|---|
| CN | 102450972 A | 5/2012 | |
| CN | 102613214 A | 8/2012 | |
| CN | 102784079 A | 11/2012 | |
| CN | 103387894 A | 11/2013 | |

(56) References Cited

FOREIGN PATENT DOCUMENTS

| | | | |
|---|---|---|---|
| CN | 103830226 A | 6/2014 | |
| CN | 103845244 A | 6/2014 | |
| CN | 103865692 A | 6/2014 | |
| CN | 104013682 A | 9/2014 | |
| EP | 1 046 390 A1 | 10/2000 | |
| EP | 1798279 A1 | 6/2007 | |
| JP | S 637785 A | 1/1988 | |
| JP | H 10218940 A | 8/1998 | |
| JP | 2000/044419 A | 2/2000 | |
| JP | 2000110099 A | 4/2000 | |
| JP | 2001087782 A | 4/2001 | |
| KR | 20110058754 A | 6/2011 | |
| RU | 2452463 C1 | 6/2012 | |
| WO | WO 94/00016 A1 | 1/1994 | |
| WO | WO 01/28340 A2 | 4/2001 | |
| WO | WO 01/32132 A2 | 5/2001 | |
| WO | WO 03/066192 A1 | 8/2003 | |
| WO | WO 03/092382 A1 | 11/2003 | |
| WO | WO 2004/010783 A1 | 2/2004 | |
| WO | WO 2004/062703 A1 | 7/2004 | |
| WO | WO 2006/085975 A2 | 8/2006 | |
| WO | WO2008/123115 A1 | 10/2008 | |
| WO | WO 2009/065023 A1 | 5/2009 | |
| WO | WO 2010/056685 A2 | 5/2010 | |
| WO | WO 2011/083401 A2 | 7/2011 | |
| WO | WO 2013/016029 A1 | 1/2013 | |
| WO | WO 2013/052545 A1 | 4/2013 | |
| WO | WO 2013/066403 A1 | 5/2013 | |
| WO | WO 2014/032696 A1 | 3/2014 | |
| WO | WO 2014/113269 A1 | 7/2014 | |
| WO | WO 2014/139904 A1 | 9/2014 | |
| WO | WO 2014/163075 | * 10/2014 | ............ A61K 8/02 |
| WO | WO 2015/166075 A1 | 11/2015 | |
| WO | WO 2016/018473 A1 | 2/2016 | |
| WO | WO 2016/018474 A1 | 2/2016 | |
| WO | WO 2016/018475 A1 | 2/2016 | |
| WO | WO 2016/018476 A1 | 2/2016 | |

OTHER PUBLICATIONS

Datasheet for WetFilm™ by Inolex, downloaded Sep. 14, 2019 from https://inolexcosmetics.ulprospector.com/en/na/personalcare/details, Year: 2019, 3 pages.
Trimethylpentanediol-adipic acid-glycerin crosspolymer—Google search Sep. 13, 2019 (Year: 2019), 2 pages.
Examination Report of Australian Patent Application No. 2014409811 dated Feb. 4, 2020; 5 pages.
Mintel GNPD, Ginkgo Green Tea Drink, 4 pages, published Sep. 2014; https://www.gnpd.com/sinatra/recordpage/2683087/?utm_source=fed_search.
Mintel GNPD, June Premium Soy Sauce, 3 pages, published Sep. 2014, https://www.gnpd.com/sinatra/recordpage/2696123/?utm_source=fed_search.
Mintel GNPD, Soy Based Sauce, 2014; 2 pages, published Sep. 2014, https://www.gnpd.com/sinatra/recordpage/2694235/?utm_source=fed_search.
Shan et al., "Antibacterial properties of Polygonum cuspidatum roots and their major bioactive constituents," ScienceDirect, Food Chemistry 109 (2008), pp. 530-537.
Google Scholar Search, "Pyrogenic Silica Antimicrobial", Aug. 3, 2020, (Year: 2020), 2 pages.
Google Scholar Search, "Pyrogenic Silica", Aug. 3, 2020 (Year: 2020), 2 pages.
Great Britain Office Action Corresponding to Application No. 1716717 dated May 7, 2021.
Draelos et al., "A New Proprietary Onion Extract Gel Improves the Appearance of New Scars," Clinical Aesthetic Dermatology, Jun. 2012, vol. 6, No. 6, p. 18-24.
CVS, "Mederma Advanced Scar Gel Ingredients", 2021, https://www.cvs.com/shop/ingredients/mederma-advanced-scar-gel-prodid-210683.
Duan et al., Naturally occurring betaine grafted on cotton fabric for achieving antibacterial and anti-protein adsorption functions, Cellulose 27, May 25, 2020, pp. 6603-6615.
Kim et al., Candidacidal Activity of Xylitol and Sorbitol, Journal of Oral Medicine and Pain, 2016, pp. 155-160.
Nalawade et al., Bactericidal activity of propylene glycol, glycerine, polyethylene glycol 400, and polyethylene glycol 1000 against selected microorganisms, Journal of International Society of Preventive and Community Dentistry, vol. 5, No. 2, 2015, pp. 114-119.
Pinazo et al., Amino acid-based surfactants: New antimicrobial agents, Advances in Colloid and Interface Science, vol. 228, 2016, pp. 17-39.
Piquero-Casals et al., Urea in Dermatology: A Review of its Emollient, Moisturizing, Keratolytic, Skin Barrier Enhancing and Antimicrobial Properties, Dermatol Ther (Heidelb) 11, 2021, pp. 1905-1915.
Romanó et al., Hyaluronic Acid and Its Composites as a Local Antimicrobial/Antiadhesive Barrier, Journal of Bone and Joint Infection, vol. 2, No. 1, 2017, pp. 63-72.
Su et al., Study on the Antimicrobial Properties of Citrate-Based Biodegradable Polymers, Frontiers in Bioengineering and Biotechnology, vol. 2, Article 23, 2014, 9 pages.

* cited by examiner

FIBROUS SUBSTRATE FOR CAPTURE OF GRAM NEGATIVE BACTERIA

RELATED APPLICATION

This application is a national phase of and claims priority to PCT/US2015/023813, filed Apr. 1, 2015, the contents of which are incorporated herein by reference thereto.

BACKGROUND OF THE INVENTION

A myriad of different types of disposable fibrous substrates are commercially available in today's marketplace. Such fibrous substrates may be in the form of wipes that may contain chemicals designed to kill microbes such as Gram negative bacteria. Such wipes can include wound care wipes, floor and furniture cleaning wipes, countertop cleaning wipes, hand, and body cleaning wipes. The common aspect of these wipes is that they contain additives or chemicals to provide an antimicrobial effect. Household kitchen countertop wipes, for example, generally contain chemicals that will kill Gram negative bacteria such as *Escherichia coli* or other microbes residing on the countertop surface.

As concern grows about allergic reactions to chemicals and about the increasing resistance of Gram negative bacteria to common antimicrobial treatments, so has the concern and desire for a wipe that avoids harsh chemicals yet still achieves its purpose. Existing wet wipes include wipes impregnated with a chemical solution such as an antimicrobial solution, where the solution helps deliver the chemicals to a contaminated surface. However, it is desirable that, after wiping the surface, the wipe retains the chemicals while removing the Gram negative bacteria from the surface. A wipe that removes the Gram negative bacteria but which does not leave chemicals on the surface being wiped would provide the desired decontamination effect without the undesirable exposure to the antimicrobial chemicals.

As such, a need currently exists for a fibrous substrate (e.g., a wipe) that is capable of removing Gram negative bacteria from a surface, without leaving substantial amounts of chemicals on the surface.

SUMMARY OF THE INVENTION

In accordance with one embodiment of the present invention, a method for removing Gram negative bacteria from a surface is provided. The method includes placing a fibrous substrate in contact with Gram negative bacteria present on the surface, wherein the fibrous substrate includes a capturing agent. The capturing agent includes a nonionic polymer having hydrophilic and lipophilic regions, and the capturing agent is present on the fibrous substrate in an amount effective to result in an increase of Gram negative bacteria present on the fibrous substrate of at least about 1 log.

In accordance with another embodiment of the present invention, a fibrous substrate for removing Gram negative bacteria from a surface is provided. The fibrous substrate includes a capturing agent, which includes a nonionic polymer having hydrophilic and lipophilic regions. The capturing agent is present on the fibrous substrate in an amount effective to result in an increase of Gram negative bacteria present on the fibrous substrate of at least about 1 log.

Other features and aspects of the present invention are discussed in greater detail below.

DETAILED DESCRIPTION OF REPRESENTATIVE EMBODIMENTS

Definitions

As used herein the term "nonwoven web" generally refers to a web having a structure of individual fibers or threads which are interlaid, but not in an identifiable manner as in a knitted fabric. Examples of suitable nonwoven webs include, but are not limited to, meltblown webs, spunbond webs, carded webs, wetlaid webs, airlaid webs, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al. Spunbond fibers are generally not tacky when they are deposited onto a collecting surface. Spunbond fibers may sometimes have diameters less than about 40 microns, and are often from about 5 to about 20 microns.

As used herein, the term "carded web" refers to a web made from staple fibers that are sent through a combing or carding unit, which separates or breaks apart and aligns the staple fibers in the machine direction to form a generally machine direction-oriented fibrous nonwoven web. Such fibers are usually obtained in bales and placed in an opener/blender or picker, which separates the fibers prior to the carding unit. Once formed, the web may then be bonded by one or more known methods.

As used herein, the term "airlaid web" refers to a web made from bundles of fibers having typical lengths ranging from about 3 to about 19 millimeters (mm). The fibers are separated, entrained in an air supply, and then deposited onto a forming surface, usually with the assistance of a vacuum supply. Once formed, the web is then bonded by one or more known methods.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a fibrous substrate that includes a capturing agent that is capable of removing Gram negative bacteria from a surface and retaining such bacteria on the fibrous substrate after a surface is contacted with the fibrous substrate. The capturing agent contains a nonionic polymer that includes both hydrophilic and hydrophobic regions, and the present inventors have discovered that when a fibrous substrate is treated with such a polymer, the fibrous substrate has a particular affinity for Gram negative bacteria. The affinity of the capturing agent disposed on the fibrous substrate for the Gram negative bacteria allows the Gram negative bacteria to be retained within or captured by the fibrous substrate such that the bacteria can be removed from a surface that is contacted with the fibrous substrate. Further, due to the affinity of the nonionic polymer having hydrophilic and lipophilic regions for the Gram negative bacteria, the presence of the polymer on the fibrous substrate inhibits the spread of the captured bacteria to other surfaces that may subsequently contact the fibrous substrate. Of particular advantage, the fibrous substrate may help protect against the spread or infection of pathogens without the use of chemicals, such as antiseptics or antibiotics.

Various embodiments of the present invention will now be described in more detail below.

I. Capturing Agent

The fibrous substrate of the present invention is treated with a capturing agent to facilitate the adherence of Gram negative bacteria to the fibrous substrate when a surface on which the Gram negative bacteria is present is contacted with the fibrous substrate. The capturing agent includes a nonionic polymer having hydrophilic and lipophilic regions. Without intending to be limited by any particular theory, it is believed that such a polymer has an enhanced affinity for Gram negative bacteria, in part due to the presence of both hydrophilic and lipophilic regions and its high molecular weight, which can help to trap or adhere bacteria that comes into contact with the fibrous substrate.

One suitable nonionic polymer having hydrophilic and lipophilic regions is a nonionic cellulose ether that includes or is modified to include both hydrophilic and lipophilic regions. For instance, in some embodiments, the nonionic cellulose can be hydrophobically modified. Suitable nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. No. 6,123,996 to Larsson, et al.; U.S. Pat. No. 6,248,880 to Karlson; and U.S. Pat. No. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as and ethyl cellulose; hydroxyalkyl cellulose ethers, such as hydroxypropyl hydroxybutyl cellulose, hydroxyethyl hydroxypropyl cellulose, hydroxyethyl hydroxybutyl cellulose, and hydroxyethyl hydroxypropyl hydroxybutyl cellulose; alkyl hydroxyalkyl cellulose ethers, such as methyl hydroxyethyl cellulose, ethyl hydroxyethyl cellulose, ethyl hydroxypropyl cellulose, methyl ethyl hydroxyethyl cellulose, and methyl ethyl hydroxypropyl cellulose; and so forth. Particularly suitable nonionic cellulosic ethers for use in the present invention are ethyl hydroxyethyl cellulose, methyl hydroxyethyl cellulose, methylethyl hydroxyethyl cellulose, and methylethyl hydroxyethyl hydroxypropyl cellulose. In such embodiments, the hydroxyethyl groups typically constitute at least 30% of the total number of hydroxyalkyl groups, and the number of ethyl substituents typically constitutes at least 10% of the total number of alkyl substituents.

Specific examples of suitable nonionic cellulose ethers having hydrophilic and lipophilic regions for use as the nonionic polymer of the present invention include $C_{12-16}$ alkyl PEG-2 hydroxypropyl hydroxyethyl ethylcellulose, which is a hydrophobically modified ethyl hydroxyethyl cellulose (HM-EHEC) commercially available under the name STRUCTURE CEL 500 HM from AkzoNobel, and methyl hydroxyethyl cellulose (MHEC), which is commercially available under the name STUCTURE CEL 8000 M from AkzoNobel.

Still another suitable nonionic polymer having both hydrophilic and lipophilic regions is a nonionic, hydrophobically modified polyacrylate. One example of such a nonionic polymer is a $C_{10\text{-}30}$ alkyl acrylate crosspolymer. The $C_{10\text{-}30}$ alkyl acrylate cross polymer is a high molecular weight cross linked poly(acrylic acid) polymer which contains a hydrophilic back bone and hydrophobic portions which stabilize the oil and lock it in place. For example, the methacrylate provides the lipophilic region, while the acrylic acid provides the hydrophilic region. One specific example of such a $C_{10\text{-}30}$ alkyl acrylate crosspolymer is commercially available under the name PEMULEN TR-2, available from Lubrizol. To render the polymer nonionic, it is to be understood that the pH of the $C_{10\text{-}30}$ alkyl acrylate crosspolymer can be adjusted such that the $C_{10\text{-}30}$ alkyl acrylate crosspolymer can have a pH below the pKa value of acrylic acid, which is about 4.3. For instance, the pH of the crosspolymer can range from about 1 to about 4, such as from about 1.25 to about 3.75, such as from about 1.5 to about 3.5.

Still another suitable nonionic polymer having both hydrophilic and lipophilic regions and contemplated by the present invention is a carbomer. Carbomers are homopolymers of acrylic acid crosslinked with an allyl ether of pentaerythritol, sucrose, or propylene. Carbomers are available from Noveon Incorporated under the tradename CARBOPOL. Examples of suitable carbomers include CARBOPOL 934, 934P, 940, 941, 954, 980, 981, 1342, 1382, 2984, and 5984; AQUA SF-1 polymer; and CARBOPOL ETD 2001 and ETD 2050; and CARBOPOL Ultrez 10.

Still another suitable nonionic polymer that has or can be modified to have hydrophilic and lipophilic regions is a modified silicone. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups.

Generally, any silicone may be used so long as it is nonionic and has both hydrophilic and lipophilic regions. In one particular embodiment, an amine-functionalized silicone can be used (i.e., an amodimethicone). In some embodiments, polydimethylsiloxane and/or modified polysiloxanes may be used as in the capturing agent of the present invention. For instance, suitable modified polysiloxanes that may be used in the present invention include, but are not limited to, phenyl-modified polysiloxanes, vinyl-modified polysiloxanes, methyl-modified polysiloxanes, alkyl-modified polysiloxanes, alkoxy-modified polysiloxanes, amino-modified polysiloxanes, and combinations thereof.

Some suitable phenyl-modified polysiloxanes include, but are not limited to, dimethyldiphenylpolysiloxane copolymers; dimethyl, methylphenylpolysiloxane copolymers; polymethylphenylsiloxane; and methylphenyl, dimethylsiloxane copolymers. Phenyl modified polysiloxanes that have a relatively low phenyl content (less than about 50 mole %) may be particularly effective in the present invention. For example, the phenyl-modified polysiloxane may be a diphenyl-modified silicone, such as a diphenylsiloxane-modified dimethylpolysiloxane. In some embodiments, the phenyl-modified polysiloxanes contain phenyl units in an amount from about 0.5 mole % to about 50 mole %, in some embodiments in an amount less than about 25 mole %, and in some embodiments, in an amount less than about 15 mole %. In one particular embodiment, a diphenylsiloxane-modified dimethylpolysiloxane may be used that contains diphenylsiloxane units in an amount less than about 5 mole %, and particularly in an amount less than about 2 mole %. The diphenylsiloxane-modified dimethylpolysiloxane may be synthesized by reacting diphenylsiloxane with dimethylsiloxane.

Besides the above-mentioned modified polysiloxanes, other modified polysiloxanes may also be utilized in the present invention. For instance, some suitable vinyl-modified polysiloxanes include, but are not limited to, vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; and vinylphenylmethyl terminated polydimethylsiloxanes. Further, some methyl-modified polysiloxanes that may be used include, but are not limited to, dimethylhydro terminated polydimethylsiloxanes; methylhydro, dimethylpolysiloxane copolymers; methylhydro terminated methyloctyl siloxane copolymers; and methylhydro, phenylmethyl siloxane copolymers. In addition, some examples of amino-modified polysiloxanes include, but are not limited to, polymethyl(3-aminopropyl)-siloxane and polymethyl[3-(2-aminoethyl) aminopropyl]-siloxane.

The particular polysiloxanes described above are meant to include hetero- or co-polymers formed from polymerization or copolymerization of dimethylsiloxane cyclics and diphenylsiloxane cyclics with appropriate endcapping units. Thus, for example, the terms "diphenyl modified dimethylpolysiloxanes" and "copoloymers of diphenylpolysiloxane and dimethylpolysiloxane" may be used interchangeably. Moreover, other examples of suitable polysiloxanes are believed to be described in U.S. Pat. No. 5,742,943 to Chen and U.S. Pat. No. 6,306,514 to Weikel, et al., which are incorporated herein in their entirety by reference thereto for all purposes. A particularly suitable modified polysiloxane for use in the present invention is an amino-modified silicone, which is commercially available under the name KF-889 from Shin Etsu Silicones of America, Inc.

Regardless of the particular capturing agent selected for application to the fibrous substrate, the capturing agent can be applied to the fibrous substrate as a component of an aqueous or nonaqueous capturing agent formulation. Although the exact quantity of the nonionic polymer having hydrophilic and lipophilic regions employed in the formulation may vary based on a variety of factors, including the presence of other additives, the suspected concentration of the microbe, etc., the nonionic polymer can typically be present in the capturing agent formulation in an amount of from about 0.01 wt. % to about 15 wt. %, in some embodiments from about 0.05 wt. % to about 10 wt. %, and in some embodiments, from about 0.1 wt. % to about 7.5 wt. % based on the total weight of the capturing agent formulation. Methods for applying the capturing agent formulation to the fibrous substrate are discussed in more detail below. Further, it is to be understood that after application of the capturing agent formulation to the fibrous substrate, the capturing agent (e.g., the nonionic polymer having hydrophilic and lipophilic regions) may constitute from about 0.1 wt. % to about 20 wt. %, in some embodiments from about 0.2 wt. % to about 15 wt. %, and in some embodiments from about 0.5 wt. % to about 10 wt. %, based on the dry weight of the fibrous substrate.

In yet another embodiment, one or more cationic polymers can be used in combination with the nonionic polymer having hydrophilic and lipophilic regions. Examples thereof include cationic cellulose, cationic dextran, cationic dextrin, cationic chitosan, cationic gelatin, cationic vinylpyrrolidone polymer, N,N-dimethyl-3,5-methylenepiperidinium chloride polymer, and distearyldimethylammoniun chloride polymer. Still other cationic polymers that can be used in combination with the nonionic polymer having hydrophilic and lipophilic regions include, for instance, polyethyleneimine, poly-L-lysine, poly(aminodoamine), poly(amino-co-ester), poly(2-N,N-dimethylaminoethylmethacrylate), high charged density polyelectrolites such as poly(methacryloxyethyl) trimethylammonium bromide poly(acrylic) acid, and epichlorohydrin-functionalized polyamines.

The nonionic polymer having hydrophilic and lipophilic regions and any optional polymers discussed above may be applied to a fibrous substrate as a capturing agent formulation that contains a mobile carrier, such as a liquid, gas, gel, etc. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide, "DMF"); etc. Upon application, the capturing agent formulation may be dried to remove the carrier and leave a residue of the capturing agent or agents. Although the actual concentration of the solvent employed will generally depend on the nature of the capturing agent and other components that may be utilized in the formulation, the solvent is nonetheless typically present in an amount from about 50 wt. % to about 99.9 wt. %, in some embodiments from about 60 wt. % to about 99 wt. %, and in some embodiments, from about 75 wt. % to about 98 wt. % of the capturing agent formulation.

In addition to cationic or anionic polymers, other additives may also be employed in the capturing agent formulation in conjunction with the nonionic polymer having hydrophilic and lipophilic regions. For instance, surfactants may be employed in certain embodiments to ensure that when applied to the fibrous substrate, the capturing agent formulation can be evenly coated. In addition, a binder may also be employed to facilitate the immobilization of the capturing agent on the fibrous substrate. The capturing agent formulation may also include various other components as is well known in the art, such as colorants, electrolytic salts, pH adjusters, fragrances, etc.

Regardless of the particular composition of the capturing agent formulation, one or more of the nonionic polymers having hydrophilic and lipophilic regions as discussed above can be used alone or in combination with the cationic or anionic polymers mentioned above to trap and/or adhere the Gram negative bacteria *Escherichia coli* to the fibrous substrate. In addition to *Escherichia coli*, other Gram negative bacteria that can be captured by the fibrous substrate of the present invention can include other Gram negative rods (e.g., *Entereobacteria, Salmonella choleraesuis, Klebsiella pneumonia, Pseudomonas aeruginosa*); Gram negative curved rods (e.g., vibious, *Heliobacter, Campylobacter*, etc.); and Gram negative cocci (e.g., *Neisseria*).

Further, it is to be understood that additional capturing agents that can adhere Gram positive bacteria such as Gram positive rods (e.g., *Bacillus, Clostridium, Listeria*, etc.) and Gram positive cocci (e.g., *Staphylococcus, Streptococcus*, etc.) are contemplated for use in the fibrous substrate of the present invention. Particularly relevant Gram positive bacteria include *Streptococcus* (Gram positive cocci), *Listeria monocytogenes* (Gram positive rod), and *Staphylococcus aureus* (Gram positive cocci). Capturing agents that can trap such Gram positive bacteria can be included in the capturing agent formulation so that the fibrous substrate can have the ability trap both Gram negative and Gram positive bacteria.

II. Fibrous Substrate

As discussed above, the capturing agent is disposed on a fibrous substrate to trap Gram negative bacteria (e.g., *E. coli*) present on a surface when such a surface (e.g., countertop, wall, table, skin, etc.) is contacted by the fibrous substrate. The fibrous substrate may be formed from any of a variety of materials that are well known in the art. In some embodiments, for example, the fibrous substrate may be a paper product containing one or more paper webs, such as a wipe, paper towel, napkin, facial tissue, bath tissue, and so forth. The particular nature of the fibrous substrate may vary depending on the intended use, and may include materials such as the nonwoven webs defined above, knitted fabrics, woven fabrics, cotton fabrics, etc.

In one embodiment, for example, the fibrous substrate can include a nonwoven web that contains an absorbent material of sufficient wet strength and absorbency for use in the desired application. For example, the nonwoven web may include absorbent cellulosic fibers formed by a variety of pulping processes, such as kraft pulp, sulfite pulp, thermomechanical pulp, etc. Such pulp fibers may be high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Washington under the trade designation of "NF-405." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, eucalyptus, maple, birch, aspen, etc. *Eucalyptus* kraft pulp fibers may be particularly desired to increase softness, enhance brightness, increase opacity, and change the pore structure of the sheet to increase its wicking ability. Further, other absorbent fibers that may be used in the present invention, such as abaca, sabai grass, milkweed floss, pineapple leaf, cellulosic esters, cellulosic ethers, cellulosic nitrates, cellulosic acetates, cellulosic acetate butyrates, ethyl cellulose, regenerated celluloses (e.g., viscose or rayon), and so forth.

Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al.

When employed, the synthetic fibers may be monocomponent or multicomponent. Multicomponent fibers are fibers that have been formed from at least two polymer components. Such fibers are usually extruded from separate extruders but spun together to form one fiber. The polymers of the respective components are usually different from each other although multicomponent fibers may include separate components of similar or identical polymeric materials. The individual components are typically arranged in substantially constantly positioned distinct zones across the cross-section of the fiber and extend substantially along the entire length of the fiber. The configuration of such fibers may be, for example, a side-by-side arrangement, a pie arrangement, or any other arrangement. Multicomponent fibers and methods of making the same are taught in U.S. Pat. No. 5,108,820 to Kaneko, et al., U.S. Pat. No. 4,795,668 to Kruege, et al., U.S. Pat. No. 5,162,074 to Hills, U.S. Pat. No. 5,277,976 to Hogle, et al., U.S. Pat. No. 5,336,552 to Strack, et al., U.S. Pat. No. 5,466,410 to Hills, U.S. Pat. No. 5,069,970 to Larqman, et al., U.S. Pat. No. 5,057,368 to Larqman, et al., U.S. Pat. No. 5,382,400 to Pike, et al., and U.S. Pat. No. 5,989,004 to Cook. When utilized, multicomponent fibers can also be splittable. In fabricating multicomponent fibers that are splittable, the individual segments that collectively form the unitary multicomponent fiber are contiguous along the longitudinal direction of the multicomponent fiber in a manner such that one or more segments form part of the outer surface of the unitary multicomponent fiber. In other words, one or more segments are exposed along the outer perimeter of the multicomponent fiber. For example, splittable multicomponent fibers and methods for making such fibers are described in U.S. Pat. No. 5,935,883 to Pike and U.S. Pat. No. 6,200,669 to Marmon, et al.

If desired, the nonwoven web material may be a composite that contains a combination of synthetic thermoplastic polymer fibers and absorbent fibers, such as polypropylene and pulp fibers. The relative percentages of such fibers may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % synthetic polymeric fibers. The nonwoven composite may likewise contain from about 40 wt. % to about 99 wt. %, in some embodiments from 50 wt. % to about 95 wt. %, and in some embodiments, from about 60 wt. % to about 90 wt. % absorbent fibers.

Nonwoven composites may be formed using a variety of known techniques. For example, the nonwoven composite may be a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, at al.; which are incorporated herein in their entirety by reference thereto for all relevant purposes.

Alternatively, the nonwoven composite may be formed be formed by hydraulically entangling fibers and/or filaments with high-pressure jet streams of water. Hydraulically entangled nonwoven composites of staple length fibers and continuous filaments are disclosed, for example, in U.S. Pat. No. 3,494,821 to Evans and U.S. Pat. No. 4,144,370 to Boulton, which are incorporated herein in their entirety by reference thereto for all purposes. Hydraulically entangled nonwoven composites of a continuous filament nonwoven web and pulp fibers are disclosed, for example, in U.S. Pat. No. 5,284,703 to Everhart, et al. and U.S. Pat. No. 6,315,864 to Anderson, at al., which are incorporated herein in their entirety by reference thereto for all purposes.

Typically, the basis weight of fibrous substrate can range from about 20 grams per square meter (gsm) to about 500 gsm, such as from about 35 gsm to about 350 gsm, such as from about 50 gsm to about 200 gsm. Lower basis weight products may be particularly well suited for use as light duty wipes, while higher basis weight products may be better adapted for use as industrial wipes.

Regardless of the particular manner by which the fibrous substrate is made, the fibrous substrate can be in the form of a wipe and may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huanq, et al.; U.S. Pat. No. 6,269,970 to Huanq, et al.; and U.S. Pat. No. 6,273,359 to Newman, et al., which are incorporated herein in their entirety by reference thereto for all purposes.

Further, regardless of the particular type of fibrous substrate utilized in the present invention, the capturing agent discussed above may be incorporated into the fibrous substrate during its formation or simply coated onto all or a portion of a surface of the fibrous substrate using known techniques, such as printing, dipping, spraying, melt extruding, coating (e.g., solvent coating, powder coating, brush coating, etc.), and so forth as a component of a capturing agent solution that can be allowed to dry on the fibrous substrate before use. If desired, the capturing agent may be applied in a pattern that covers from about 5% to about 95%, in some embodiments from about 10% to about 90%, and in some embodiments, from about 20% to about 75% of a surface of fibrous substrate. The patterned application of the capturing agent may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance.

A variety of techniques may be used for applying the capturing agent in the desired pattern. For instance, the capturing agent may be applied to the fibrous substrate using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable electronic engraved example for a primary delivery zone is about 200 deposits per lineal inch of surface, or about 40,000 deposits per square inch. By providing such a large number of small deposits, the uniformity of the deposit distribution may be enhanced. Also, because of the large number of small deposits applied to the surface of the fibrous substrate, the deposits more readily resolidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the fibrous substrate upon which the capturing agent is to be printed. For instance, the capturing agent can be painted onto the screen in the form of a solution, and transferred by rubbing the screen (which is in contact with the fibrous substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc.

In addition to the printing techniques mentioned above, any other suitable application technique may be used in the present invention to treat the fibrous substrate with the capturing agent. For example, other suitable printing techniques may include, but are not limited to, laser printing, thermal ribbon printing, piston printing, spray printing, flexographic printing, etc. Still other suitable application techniques may include bar, roll, knife, curtain, spray, slot-die, dip-coating, drop-coating, extrusion, or stencil application, etc. Such techniques are well known to those skilled in the art.

As a result of the present invention, it has been discovered that a fibrous substrate including a capturing agent (e.g., a nonionic polymer having hydrophilic and lipophilic regions) may be employed to remove Gram negative bacteria (*Escherichia coli*) from a surface (e.g., countertop, wall, table, skin, etc). In particular, upon contacting the fibrous substrate with a surface on which the Gram negative bacteria is present, a log increase in bacteria present on the fibrous substrate may be observed. For instance, the fibrous substrate may exhibit an increase of bacteria present on the fibrous substrate of at least about 1 log, in some embodiments at least about 2 log, in some embodiments at least about 3 log, in some embodiments, at least about 4 log, and in some embodiments at least about 5 log (e.g., about 10 or 11 log), indicating that the substrate is trapping bacteria removed from the contacted surface, as represented by the increase in bacteria present on the fibrous substrate. Log increase, for example, may be determined from the fold increase bacteria adhered to or captured by the fibrous substrate according to the following correlations:

| Fold Increase of Bacteria | Log Increase |
|---|---|
| 10 | 1 |
| 100 | 2 |
| 1000 | 3 |
| 10,000 | 4 |
| 100,000 | 5 |
| 1,000,000 | 6 |
| 10,000,000 | 7 |
| 100,000,000 | 8 |
| 1,000,000,000 | 9 |
| 10,000,000,000 | 10 |
| 100,000,000,000 | 11 |
| 1,000,000,000,000 | 12 |

In other words, a fibrous substrate exhibiting an increase of bacteria of 1 log means the number of bacteria on the fibrous substrate has increased 10-fold, an increase of 2 log means the number of bacteria has increased 100-fold, an increase of 3 log means the number of bacteria has increased 1000-fold, an increase of 4 log means the number of bacteria has increased 10,000-fold, an increase of 5 log means the number of bacteria has increased 100,000-fold, an increase of 6 log means the number of bacteria has increased 1,000,000-fold, etc., as compared to the number of bacteria present on a fibrous substrate that is not treated with a capturing agent. A larger log increase thus corresponds with a fibrous substrate that is able to more effectively trap Gram negative bacteria.

The present invention may be better understood with reference to the following examples.

Example 1

The attachment of Gram negative *Escherichia coli* to a polystyrene surface treated with various compounds was measured in terms of log reduction after 15 minutes of adhesion time. Thus, a negative log reduction corresponds with a log increase of bacteria adhered to or captured by the polystyrene surface, while a positive log reduction corresponds with a log decrease of bacteria adhered to or captured by the polystyrene surface. The results are shown in Table 1 below.

TABLE 1

| Compound No. | Compound Type | Compound Name | Wt. % in Formulation | pH | INCI Name | Log Reduction of *E. coli* (ATCC 11229) |
|---|---|---|---|---|---|---|
| 1 | Polysaccharide | Structure Cel 8000M | 1.5% | | Methyl Hydroxyethyl Cellulose (MHEC) | −11.4 |
| 2 | Silicone | KF 889s | 5.0% | | Amodimethicone | −8.4 |
| 3 | Synthetic polymer | Ultrez 10 | 5.0% | 4.4 | Carbomer | −5.8 |
| 4 | Polysaccharide | Structure Cel 500 HM | 3.0% | | $C_{12-16}$ Alkyl PEG-2 Hydroxypropyl Hydroxyethyl Ethylcellulose | −4.2 |

TABLE 1-continued

| Compound No. | Compound Type | Compound Name | Wt. % in Formulation | pH | INCI Name | Log Reduction of E. coli (ATCC 11229) |
|---|---|---|---|---|---|---|
| 5 | Synthetic Polymer | Pemulen TR-2 | 0.2% | 3.39 | $C_{10-30}$ Alkyl Acrylate Crosspolymer | −1.0 |
| 6 | Synthetic Polymer | Pemulen TR-2 | 0.2% | 6.30 | $C_{10-30}$ Alkyl Acrylate Crosspolymer | −0.9 |
| 7 | Synthetic Polymer | Pemulen TR-2 Neutralized | 0.2% | | $C_{10-30}$ Alkyl Acrylate Crosspolymer | −0.3 |
| 8 | Silicone | Silsoft 440 | 5.0% | | PEG20/PPG23 Dimethicone | 0.0 |
| 9 | Synthetic Polymer | Ultrez 20 | 0.1% | | Acrylate/$C_{10-30}$ Alkyl Acrylate Crosspolymer | 0.0 |
| 10 | Silicone | Silsurf T 208 | 2.5% | | PEG-8 Dimethicone | 0.3 |
| 11 | Silicone | DC 193 | 5.0% | | PEG-12 Dimethicone | 0.6 |
| 12 | Silicone | Siliamine C300 | 5.0% | | Dimethicone PEG-8 Amine | 0.6 |
| 13 | Synthetic Polymer | Cevcol 540 S | 3.0% | | Polyvinyl Alcohol | 1.6 |
| 14 | Silicone | DC 1501 | 100.0% | | Cyclopentasiloxane (and) Dimethiconol | 1.9 |
| 15 | Polysaccharide | HPMC | 3.0% | | Hydroxy Propyl Methyl Cellulose | 2.5 |

As shown in Table 1, Compounds 1-5, the polystyrene surfaces treated with a methyl hydroxyethyl cellulose (MHEC), an amine-functionalized silicone, a carbomer, a $C_{12-16}$Alkyl PEG-2 Hydroxypropyl Hydroxyethyl Ethylcellulose, and a $C_{10-30}$ alkyl acrylate crosspolymer having a pH below the pKa value of acrylic acid (i.e., below about 4.3), which are nonionic polymers having hydrophilic and lipophilic regions, showed at least about a 1 log increase (i.e., at least about a −1 log reduction) in the amount of *Escherichia coli* present on the polystyrene surface after about 15 minutes as compared to a control. In contrast, treating a polystyrene surface with Compound 13, which is a nonionic hydrophilic polymer, did not result in an increase in the amount of *Escherichia coli* present on the polystyrene surface and instead a 1.6 log decrease in the amount of *Escherichia coli* present on the polystyrene surface was observed for Compound 13.

Example 2

The attachment of Gram positive *Staphylococcus aureus* to a polystyrene surface treated with various compositions including different compounds was measured in terms of log reduction after 15 minutes of adhesion time. Thus, a negative log reduction corresponds with a log increase of bacteria adhered to or captured by the polystyrene surface, while a positive log reduction corresponds with a log decrease of bacteria adhered to or captured by the polystyrene surface. The results are shown in Table 2 below.

TABLE 2

| Compound No. | Compound Type | Compound Name | Wt. % in Formulation | pH | INCI Name | Log Reduction of S. aureus (ATCC 6538) |
|---|---|---|---|---|---|---|
| 1 | Synthetic Polymer | Pemulen TR-2 | 0.20% | 6.3 | $C_{10-30}$ Alkyl Acrylate Crosspolymer | −3.2 |
| 2 | Synthetic Polymer | Ultrez 10 | 5.0% | 4.4 | Carbomer | −2.8 |
| 3 | Synthetic Polymer | Pemulen TR-2 | 0.20% | 7.3 | $C_{10-30}$ Alkyl Acrylate Crosspolymer | −0.9 |
| 4 | Synthetic Polymer | Pemulen TR-2 | 0.20% | 5.4 | $C_{10-30}$ Alkyl Acrylate Crosspolymer | −0.4 |
| 5 | Synthetic Polymer | Pemulen TR-2 Neutralized | 0.20% | | $C_{10-30}$ Alkyl Acrylate Crosspolymer | −0.1 |
| 6 | Synthetic Polymer | Ultrez 20 | 0.10% | | Acrylate/$C_{10-30}$ Alkyl Acrylate Crosspolymer | −0.1 |

As shown in Table 2, the polystyrene surfaces treated with a $C_{10-30}$ alkyl acrylate crosspolymer or a carbomer showed an increase (i.e., a negative log reduction ranging from −0.1 at the low end to −3.2 at the high end) in the amount of *Staphylococcus aureus* present on the polystyrene surface after about 15 minutes as compared to a control.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for removing Gram negative bacteria from a surface, the method comprising placing a fibrous substrate in contact with Gram negative bacteria present on the surface, wherein the fibrous substrate comprises absorbent pulp fibers, synthetic thermoplastic fibers and a capturing agent formulation comprising a capturing agent and a carrier, wherein the capturing agent comprises a nonionic amine-functionalized silicone polymer having hydrophilic and lipophilic regions, wherein the capturing agent is incorporated into the fibrous substrate during formation or coated onto all or a portion of a surface of the fibrous substrate, and is present in or on the fibrous substrate in an amount effective to result in an increase of Gram negative bacteria present on the fibrous substrate of at least about 1 log;
   wherein the nonionic amine-functionalized silicone polymer having hydrophilic and lipophilic regions is polymethyl(3-aminopropyl)-siloxane or polymethyl[3-(2-aminoethyl)aminopropyl]-siloxane;
   wherein the fibrous substrate is a wipe;
   wherein the capturing agent is free of an acrylic acid polymer; and
   wherein the capturing agent formulation is free from water and alcohol.

2. The method of claim 1, wherein the capturing agent further comprises a nonionic cellulose ether, a carbomer, a modified silicone, or a combination thereof.

3. The method of claim 1, wherein the capturing agent further comprises a hydrophobically modified ethyl hydroxyethyl cellulose or a methyl hydroxyethyl cellulose.

4. The method of claim 1, wherein the nonionic amine-functionalized silicone polymer having hydrophilic and lipophilic regions constitutes from about 0.1 wt. % to about 20 wt. % of the dry weight of the fibrous substrate.

5. The method of claim 1, wherein the Gram negative bacteria is *Escherichia coli*.

6. A fibrous substrate for removing Gram negative bacteria from a surface, the fibrous substrate comprising absorbent pulp fibers, synthetic thermoplastic fibers and a capturing agent formulation comprising a capturing agent and a carrier, wherein the capturing agent comprises a nonionic amine-functionalized silicone polymer having hydrophilic and lipophilic regions, wherein the capturing agent is incorporated into the fibrous substrate during formation or coated onto all or a portion of a surface of the fibrous substrate and is present in or on the fibrous substrate in an amount effective to result in an increase of Gram negative bacteria present on the fibrous substrate of at least about 1 log;
   wherein the nonionic amine-functionalized silicone polymer having hydrophilic and lipophilic regions is polymethyl(3-aminopropyl)-siloxane or polymethyl[3-(2-aminoethyl)aminopropyl]-siloxane;
   wherein the fibrous substrate is a wipe;
   wherein the capturing agent is free of an acrylic acid polymer; and
   wherein the capturing agent formulation is free from water and alcohol.

7. The fibrous substrate of claim 6, wherein the capturing agent further comprises a hydrophobically modified ethyl hydroxyethyl cellulose or a methyl hydroxyethyl cellulose.

8. The fibrous substrate of claim 6, wherein the capturing agent constitutes from about 0.1 wt. % to about 20 wt. % of the dry weight of the fibrous substrate.

9. The fibrous substrate of claim 6, wherein the capturing agent is present on a surface of the fibrous substrate in a pattern that covers from about 5% to about 95% of the surface of the fibrous substrate.

10. The fibrous substrate of claim 6, wherein the Gram negative bacteria is *Escherichia coli*.

11. The fibrous substrate of claim 6, wherein the capturing agent is coated onto all or a portion of a surface of the fibrous substrate using gravure printing, screen printing, or ink-jet printing.

12. The fibrous substrate of claim 6, wherein the fibrous substrate comprises from about 1 wt. % to about 60 wt. % of synthetic thermoplastic fibers.

13. The fibrous substrate of claim 12, wherein the fibrous substrate comprises from about 10 wt. % to about 40 wt. % of synthetic thermoplastic fibers.

14. The fibrous substrate of claim 6, wherein the wipe comprises a coform material.

15. The fibrous substrate of claim 6, wherein the fibrous substrate is hydroentangled.

16. The fibrous substrate of claim 6, wherein a basis weight of the fibrous substrate is from about 20 grams per square meter (gsm) to about 500 gsm.

17. The fibrous substrate of claim 16, wherein the basis weight is from about 50 gsm to about 200 gsm.

18. The fibrous substrate of claim 6, wherein the capturing agent is coated on all or a portion of a surface of the fibrous substrate in a pattern.

19. The fibrous substrate of claim 6, wherein the increase of Gram negative bacteria present on the fibrous substrate is at least about 5 log.

* * * * *